United States Patent
Libanati et al.

(10) Patent No.: US 6,896,876 B1
(45) Date of Patent: May 24, 2005

(54) HIGH CLEANING SILICA GEL DENTAL ABRASIVE, DENTIFRICES PREPARED THEREFROM, AND A METHOD FOR PREPARING THE DENTAL ABRASIVE

(75) Inventors: Cristian Libanati, Silver Spring, MD (US); James George Miller, Ellicott City, MD (US); Sandra Joan Kempske, Towson, MD (US)

(73) Assignee: W.R. Grace & Co.-Conn., Columbia, MD (US)

( * ) Notice: Subject to any disclaimer, the term of this patent is extended or adjusted under 35 U.S.C. 154(b) by 0 days.

(21) Appl. No.: 10/062,602

(22) Filed: Jan. 31, 2002

Related U.S. Application Data

(60) Provisional application No. 60/265,398, filed on Jan. 31, 2001.

(51) Int. Cl.$^7$ .............................. A61K 7/16; C01B 33/12
(52) U.S. Cl. ................. 424/49; 423/335; 423/338; 423/339; 516/102; 516/111; 51/308
(58) Field of Search ..................... 424/48–58; 423/335, 423/338, 339; 516/102, 111; 51/308

(56) References Cited

U.S. PATENT DOCUMENTS

| | | | |
|---|---|---|---|
| 3,670,076 A | 6/1972 | Muhler | 424/157 |
| 3,957,968 A | 5/1976 | Cordon | 424/57 |
| 4,303,641 A | 12/1981 | DeWolf, II et al. | 424/49 |
| 5,589,160 A | 12/1996 | Rice | 424/49 |
| 5,651,958 A | 7/1997 | Rice | 424/49 |
| 5,939,051 A | 8/1999 | Santalucia et al. | 424/49 |
| 6,290,933 B1 * | 9/2001 | Durga et al. | 424/49 |
| 6,416,744 B1 * | 7/2002 | Robinson et al. | 424/48 |

FOREIGN PATENT DOCUMENTS

| | | | |
|---|---|---|---|
| WO | WO 99/51196 | 10/1999 | A61K/7/16 |

* cited by examiner

*Primary Examiner*—Frederick F. Krass
(74) *Attorney, Agent, or Firm*—William D. Bunch

(57) ABSTRACT

A silica gel abrasive having good cleaning and low abrasion is prepared by combining at least two silica gels before adjusting the pH of the abrasive to a pH in the range of 3–6. One of the gels is washed at relatively lower temperature compared to the wash temperature of a second gel. The two gels are then milled and dried to a median particle size in the range of 5 to 12 microns. The volatiles content of the gel combination is in the range of 20–40% by weight. The resulting mixtures have low abrasion as measured by Einlehner, e.g., in the range of 0.5 to 3 when measured using a brass screen. A dentifrice composition comprising 10 to 25% of the abrasive has a PCR of at least 80 and can obtain PCR's greater than 100.

11 Claims, 1 Drawing Sheet

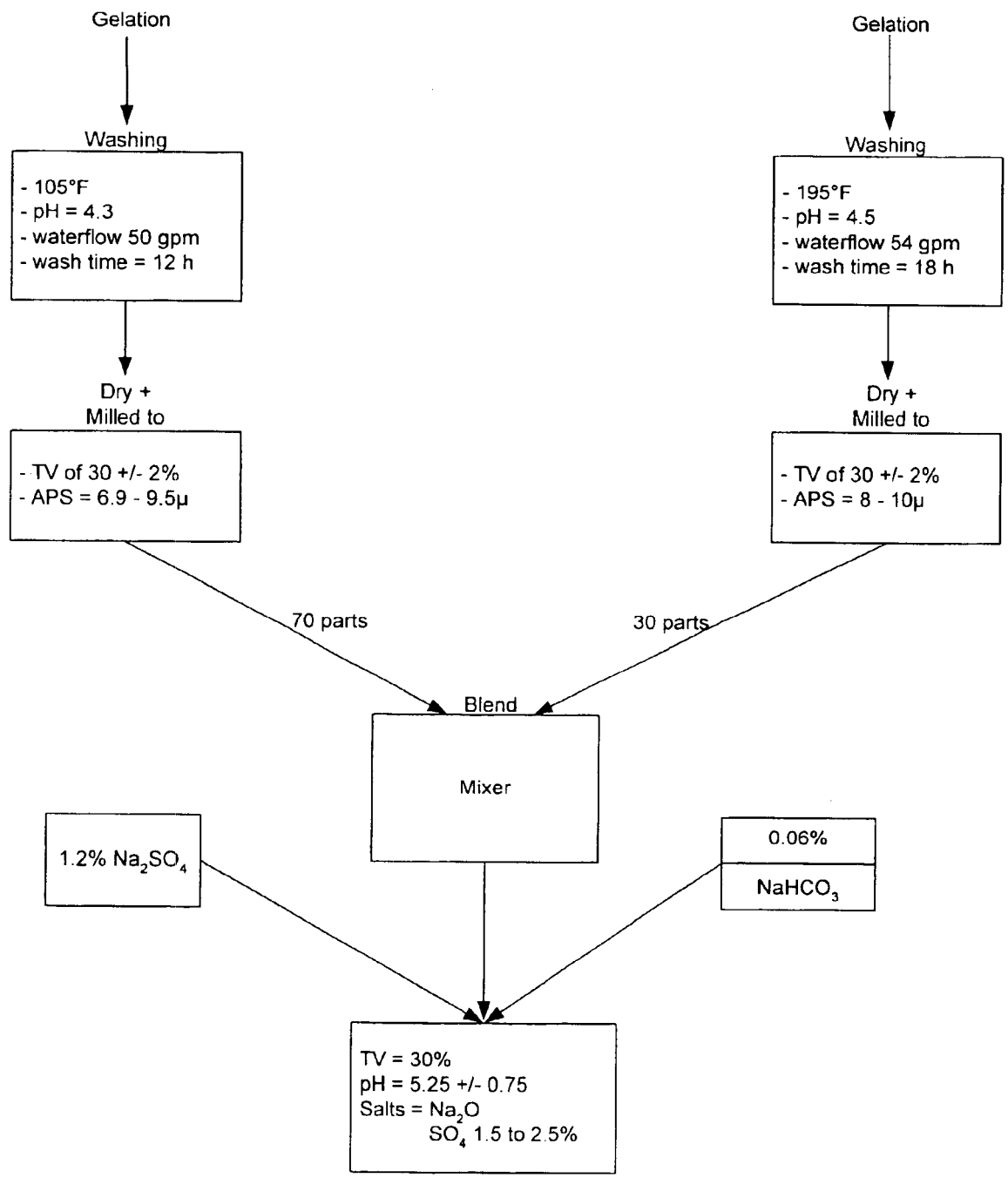
Figure

HIGH CLEANING SILICA GEL DENTAL ABRASIVE, DENTIFRICES PREPARED THEREFROM, AND A METHOD FOR PREPARING THE DENTAL ABRASIVE

This application claims the benefit of U.S. Provisional Application No. 60/265,398, filed Jan. 31, 2001.

BACKGROUND OF THE INVENTION

1. Field of the Invention

This invention relates to silica compositions useful as an abrasive in a dentifrice and methods for making the same. The invention also relates to dentifrices, preferably toothpastes, which effectively clean teeth without a high degree of dentin and/or enamel abrasion.

2. Relevant Art

Dentifrices, e.g., such as toothpastes, are used to clean teeth. Abrasive substances are formulated in the toothpaste as the primary cleaning agent. In particular, such dentifrices aid in the removal of food particles, the removal of discoloration caused by substances such as tobacco or tea, and the removal of firmly adhering bacterial films, referred to as plaque, from the surface of the teeth.

To achieve cleaning, the abrasive in dentifrices have to provide a certain degree of abrasiveness with respect to the surface of the teeth. It is important, however, that abrasiveness with respect to dental enamel and dentine be at an acceptably low level to prevent the surface of the teeth from being damaged by the daily use of the toothpaste. The rate of enamel removal through brushing should not exceed the rate at which it is replenished through natural remineralization processes.

The abrasive used should also be compatible with the other components of the toothpaste. It should lend itself to processing with water, humectants and consistency regulators to form a ductile paste readily dispensable from tubes or dispensers. It also should not adversely affect known caries inhibitors, for example, fluoride carriers, such as NaF or Na monofluorophosphate, even in the event of prolonged storage.

U.S. Pat. No. 3,957,968, discloses tooth pastes containing a combination of alpha-aluminum oxide (corundum) and a second abrasive having a Mohs hardness of less than about 6 which are said to have good cleaning and polishing effects. Alpha-aluminum oxide, however, has a Mohs hardness of 9, and has a relatively strong abrasive effect on dental enamel. To reduce the enamel abrasion, certain calcium, magnesium or sodium salts have been added to a dentifrice containing the aforementioned abrasives.

U.S. Pat. No. 4,303,641 discloses an alkaline treatment for increasing the abrasiveness, and as a result its cleaning performance, of dentifrice silica gel compositions. The process described in this patent does not require employing the processing and drying steps typically used to prepare prior art gels. It also discloses that treating silica gels with alkaline materials enhances the cleaning performance of the gels as evidenced by increased Radioactive Dentine Abrasion (RDA), defined later below. The Examples in the '641 patent illustrate the alkaline treatment on gels having average particle sizes greater than 10 microns, e.g., about 14–16 microns. The RDA values shown for these alkaline treated gels, however, are quite high as evidenced by "powder" RDA's which this patent reports to be over 1,000 (and over 200 if measured using RDA methods disclosed herein) for some samples. This indicates that the alkaline treated gels exhibit a high degree of abrasiveness on dentin surfaces.

Non-alkaline treated silica xerogel abrasives are also well known in the art. Such gels typically have particle sizes from 10 to 50 microns, depending on the 'grittiness' desired. The aforementioned '641 patent discloses that non-alkaline treated silica gels are effective polishing and cleaning agents while causing low amounts of damage to underlying tooth materials such as dentin and enamel. However, the '641 patent also discloses that more effective cleaning is achieved via alkaline treatment of such silica gels.

U.S. Pat. No. 5,651,958 discloses using a combination of specific silicas in dentifrices to balance cleaning with minimal abrasion to dentin and enamel surfaces. The '958 patent discloses combining precipitated silica having a narrow particle size range distribution of soft particles having a mean value ranging from 8 to 14 microns with a silica gel in which 70% of the gel particles have a diameter below 25 microns and a Radioactive Dentin Abrasion from 62 to about 100. The silica gel particles described in this patent have an Einlehner hardness from about 3 to about 15 as measured using a brass screen.

U.S. Pat. No. 5,589,160 discloses using a combination of two precipitated silicas as a dentifrice abrasive. One of the precipitated silicas has a mean particle size of about 5 to 11 microns and an Einlehner hardness of 0.8 to 2.5 as measured using a brass screen. The other precipitated silica has a mean particle size of from about 5 to about 11 and an Einlehner hardness from about 3 to about 8 as measured using a brass screen.

U.S. Pat. No. 3,670,076 discloses a combination of relatively small and large alumina particles as providing superior abrasives and cleaning.

U.S. Pat. No. 5,939,051 also discloses silica gel abrasives which impart good cleaning properties to dentifrice compositions, but results in relatively low abrasion. The preferred abrasive, which is identified as XWA 300 from W. R. Grace & Co.-Conn., has a relatively small particle size, e.g., 2 to 4 microns. WO 99/51196 discloses a similar abrasive. That abrasive is obtained by sustained milling which in turn results in substantial drying. As a result these particles are somewhat more expensive to make. They also typically have a volatiles content of 20% or less. The most preferred cleaning and abrasivity performance using the XWA 300 abrasive is obtained by combining it with a larger, less abrasive silica gel having particle sizes of 12 microns or greater. See WO 99/51196.

The above-mentioned measures, however, have not completely solved the problem of obtaining effective cleaning without the excessive abrasion of dental enamel. Workers in the art have continued to search for dentifrices containing abrasive systems which have reduced abrasion of dental enamel, but still effect acceptable cleaning.

SUMMARY OF THE INVENTION

The composition of this invention is a relatively good cleaning abrasive, but also exhibits acceptable low levels of abrasion. The abrasive is amorphous silica gel comprising particulate having:

(a) a median particle size in the range of about 5 to 12 microns;

(b) bronze screen Einlehner hardness of about 0.1 to 3;

(c) total volatile content of 20 to about 40% by weight based on the weight of silica; and (d) pH of about 3.0 to 6.

The abrasive properties of the composition are reflected in Einlehner measurements using a bronze screen. The Einlehner measurements for the invention when determined using that screen are less than 3, compared to a range of 3 to 8 for other abrasives as obtained using a brass screen. Moreover, the composition can consist essentially of silica gel. The performance of the invention does not rely on an additional type of abrasive such as a precipitated silica or alumina. When the invention is incorporated into a conventional dentifrice, the dentifrice has good cleaning properties as measured by the Pellicle Cleaning Ratio (PCR). Dentifrice containing the invention have a PCR of at least 80 and preferably about 100 or greater.

The composition is made by combining at least two silica gel stocks which have been washed, dried and then blended. The final abrasive gel has a pH of about 3.0 to 6.0.

BRIEF DESCRIPTION OF THE DRAWING

The FIGURE illustrates an embodiment of the process used to the make the abrasive particles of the invention.

DETAILED DESCRIPTION OF THE INVENTION

The gels used to make the invention can be conventional acid set silica hydrogels. A suitable gel is described in U.S. Pat. No. 4,474,824 to Dewolf, the contents of which are incorporated herein by reference. More specifically, acid set silica hydrogels may be produced by reacting an alkali metal silicate and a mineral acid in an aqueous medium to form a silica hydrosol and allowing the hydrosol to set to a hydrogel. When the quantity of acid reacted with the silicate is such that the final pH of the reaction mixture is acidic, the resulting product is considered an acid-set hydrogel. Sulfuric acid is the most commonly used acid, although other mineral acids such as hydrochloric acid, nitric acid, or phosphoric acid may be used. Sodium or potassium silicate may be used, for example, as the alkali metal silicate. Sodium silicate is preferred because it is the least expensive and most readily available. The concentration of the aqueous acidic solution is generally from about 5 to about 70 percent by weight and the aqueous silicate solution commonly has an $SiO_2$ content of about 6 to about 25 weight percent and a weight ratio of $SiO_2$ to $Na_2O$ of from about 1:1 to about 3.4:1.

The mineral acid solution and the alkali metal silicate solution are mixed to form a silica hydrosol. The relative proportions and concentrations of the reactants are controlled so that the hydrosol contains about 6 to about 20 weight percent $SiO_2$ and is at a pH of less than about 5 and commonly between about 1 to about 3. Generally, continuous processing is employed and both reactants are metered separately into a high speed mixer. The reaction may be carried out at any convenient temperature, for example, from about 15 to about 80° C. and is generally carried out at ambient temperatures.

The silica hydrosol will set to a hydrogel in generally about 5 to about 90 minutes and is then washed with an aqueous acidic solution to remove residual alkali metal salts which are formed in the reaction. For example, when sulfuric acid and sodium silicate are used as the reactants, sodium sulfate is entrapped in the hydrogel. Prior to washing, the gel is normally cut or broken into pieces in a particle size range of from about ½ to about 3 inches. The gel may be washed with an aqueous solution of mineral acid such as sulfuric acid, hydrochloric acid, nitric acid, or phosphoric acid or a medium strength acid such as formic acid, acetic acid, or propionic acid.

The wash solution contains an amount of the acid sufficient to provide a pH of from about 2.0 to about 5.0, preferably from about 2.5 to about 4.5. The temperature of the wash solution affects the properties of the hydrous silica gel product. Generally, the temperature of the solution is from about 80° to about 200° F. For one of the gels of this invention, the wash solution should be at a temperature of from about 80° to about 130° F. in order to enhance further the abrasiveness of the hydrous silica gel product. This is referred to below as the first gel. It is believed that lower wash temperatures reduce bonding between micelles and facilitate shrinkage on subsequent drying.

The gels of this invention are washed for a period sufficient to reduce the total salts content to less than about 5 weight percent. The gel may have, for example, a $Na_2O$ content of from about 0.5 to about 3 weight percent and a $SO_4$ content of from about 0.05 to about 3 weight percent, based on the dry weight of the gel. The period of time necessary to achieve this salt removal varies with the flow rate of the wash medium and the configuration of the washing apparatus. Generally, the period of time necessary to achieve the desired salt removal is from about 6 to about 30 hours. Although the effect is not as great as that of decreased wash temperatures, shorter washing periods increase the abrasiveness of the hydrous silica gel products because bonding between micelles is further reduced and thus shrinkage on subsequent drying is enhanced. Thus, the first gel of the invention is preferably washed with the aqueous acidic solution at a temperature of from about 80° to about 130° F. for about 6 to about 15 hours, especially for about 6 to about 12 hours.

The gel pH increases as the salts are removed by the acid wash. In order to prepare hydrous silica gels suitable for use in the dentifrice compositions of this invention, the final gel pH upon completion of washing as measured in a 5 weight percent aqueous slurry of the gel, may range from about 2.5 to about 5.

To the first gel is added to at least one other gel. The other gel can be the same acid set gel prepared according to the method above, except the other gel is washed under different conditions, e.g., at higher temperatures and longer residence time. The other gel is preferably washed at a temperature in the range of 110–200° F. for 12 to 20 hours.

The first gel and other gel(s) are dried and milled to the desired particle size. In the examples below, two gels are dried and milled separately. The gels are milled and dried using standard milling equipment such as air mills. The first gel can be milled to a median particle size in the range of about 6 to 10 microns, as measured by Malvern, and the second gel to a median particle size in the range of about 8 to 12 microns. The two gets are then combined and blended in a mixer.

The blend may also require being treated with an alkaline substance to obtain a pH of about 2.5 to 6. If used, the alkaline substance is added after the gels have been milled. The alkaline compound used in the aforementioned treatment is preferably sodium bicarbonate, but other known alkalines such as sodium carbonate, sodium hydroxide, ammonia and potassium hydroxide, can be used. The above-referenced pH is measured in water at 5% by weight silica.

While the gels in the examples below are milled and dried separately, the invention can also be prepared by combining two separately washed gels and then milling and drying them, for example, to a median particle size in the range of 5 to 12 microns.

The milling and drying conditions are selected to result in a gel having a volatiles content of about 20 to about 40% based on the weight of the silica. The term "volatiles content" is used herein to refer to any solvent contained within the pore structure of the gel. Hydrogels typically contain aqueous solvents such as the aqueous wash solutions mentioned above. The volatiles contents (TV) referred to herein are calculated by the following formula:

$$TV = 100 \times \left[ \frac{Gel(\text{as is, gm}) - Gel(db, \text{gm})}{Gel(\text{as is, gm})} \right]$$

Gel (db) is the weight in grams of the gel after ignition at 1750° F.

The milling conditions depend on the mill selected and whether drying and milling are conducted simultaneously. The aforementioned '824 patent to Dewolf discloses various conditions which can be manipulated to affect volatiles content when using a rotary drier after milling. The gels can also be milled and dried simultaneously using an impact mill in which heated air is introduced. The relevant portions of the DeWolf patent for milling and drying when using such mills is incorporated herein by reference.

The abrasive of this invention can be incorporated into a dentifrice using convention techniques. The abrasive can comprise 1 to 99% of the total dentifrice composition. The abrasive of the invention preferably comprises 10 to 25% of the total dentifrice when the abrasive is used in a paste.

In a preferred embodiment, the dentifrice is in the form of a paste, and in this event it will comprise the abrasive silica, humectant and a binder in amounts to give the dentifrice a smooth texture and good flowability. Suitable humectants and binders are known in the art. Suitable humectants include glycerin, sorbitol, ethyl alcohol, mineral oil, corn syrup, glucose and invert sugars, glycols and honey. Glycerin and sorbitol are preferred. Suitable binders include gum tragacanth, sodium carboxymethylcellulose, hydroxyethylcellulose, Indian gum, Irish moss or carrageenan and its derivatives, starch, acacia gums, locust bean gum, pectin and petrolatum.

The dentifrice of the invention can also contain as optional ingredients a soap or synthetic detergent as a surface tension depressant; flavoring materials; buffers; sweeteners such as saccharin; humectants; preservatives; thixotropic agents such as pyrogenic silica, and harmless coloring materials, in various proportions to give any desired effect. A fluoride such as stannous fluoride, sodium fluoride, sodium monofluorophosphate, zirconium fluoride, or sodium fluosilicate can be included. Each of these fluorine compounds contains available fluoride which can be taken up by the enamel of the teeth. Compounds that are capable of calcium chelation such as phosphates and pyrophosphates are also frequently included constituents of commercial dentifrice formulations. These are conventional components of dentifrices, and materials suitable for this purpose need not be enumerated for they are well known to those skilled in the dentifrice art. U.S. Pat. No. 5,589,160 provides an extensive list of dentifrice components and the contents of that patent are incorporated herein by reference.

Additional abrasives, e.g., silica gel abrasives sold as Sylodent® 783 abrasive from W. R. Grace & Co.-Conn., may also be used. In a preferred embodiment illustrated below, the invention is used at a 1:1 ratio with an additional abrasive.

The silica gels of the invention also permit the incorporation of oral health agents such as germicides, antibiotics and astringents. Typical examples include tyrothrycin, triclosan, chlorophyllins, hexachlorophene, the sarcosides and astringent salts.

Any oral health agents are employed in the dentifrice at a beneficial amount normally ranging from about 0.01 percent to about 2 percent by weight of paste dentifrice. The humectants are generally employed in an amount from about 5 percent to about 75 percent by weight of the dentifrice, the binders in an amount from about 0.5 percent to about 30 percent by weight of the dentifrice, flavoring agents in an amount from about 0.1 percent to about 5 percent by weight of the dentifrice, water in an amount from about 4 percent to about 60 percent by weight of the dentifrice, surface tension depressants in an amount from about 0.01 percent to about 6 percent by weight of the dentifrice, and preservatives in an amount from about 0.01 percent to about 2 percent of the dentifrice. The dentifrices are prepared by blending the components together, with deaeration being necessary for the translucent and transparent toothpastes.

The unexpected cleaning performance for this invention is shown using conventional cleaning and abrasive tests. For example, dentifrice compositions are typically screened in vitro using the "Stookey Cleaning Test" to determine a composition's efficacy for cleaning and stain removal. This test performs a simulated brushing action typically on more readily available bovine teeth which have been artificially stained. The removal of stain after a brushing operation is quantified by measuring the decrease in color (or blackness) using a calorimeter. Rather than comparing absolute changes in color, the data are usually referenced to that of American Dental Association reference material calcium pyrophosphate (that is, the stain reduction resulting from calcium pyrophosphate use is taken to be by definition 100). Therefore, the cleaning performance of the test compositions will be either below (<100), equal to (=100), or higher (>100) than that obtained using calcium pyrophosphate. This normalized cleaning value is often called the Pellicle Cleaning Ratio (PCR). The higher the PCR the greater the stain removal or "whitening".

The relatively low abrasion shown by the invention is reflected in Einlehner numbers obtained from the powder abrasive per se. Einlehner hardness values are measured using an Einlehner At-1000 Abrader to measure the softness of the silicas in the following manner: A bronze wire screen is weighed and exposed to the action of a 10% aqueous silica suspension for a certain length of time. The amount of abrasion is then determined as milligrams weight lost of the bronze wire screen per 100,000 revolutions. The results are expressed in milligrams.

Radioactive Dentin Abrasion (RDA) testing may also be used to measure how the abrasive nature of a dentifrice composition contributes to removal of the softer dentin tissue of the tooth structure. In this test, irradiated dentin is brushed in a manner similar to that described above for cleaning. The amount of dentin that is abraded away from the brushed structure is quantified via radioactive analysis of $^{32}P$ which is observed in the abrasive slurry. In a manner similar to that described for cleaning, the amount of dentin abrasion is referenced to that which occurs with calcium pyrophosphate which is likewise set at 100. The lower the RDA the less abrasive the dentifrice composition.

The following examples of the invention are illustrative and are not intended to limit in any way the invention as recited in the appended claims.

EXAMPLE 1

Preparing the Invention

A silica gel (1) is prepared by washing a silica hydrosol under acidic (pH=4.0) conditions at 105° F. for thirteen hours. The resulting gel is then dried to a 30% total volatiles content and milled to approximately 9 micron average particle size. A second gel (2) is prepared by washing a silica hydrosol under acidic conditions (pH=4–5) at 195° F. for eighteen hours. The gel is then simultaneously dried and milled to 30% total volatiles content and approximately 9 micron average particle size.

The two silica gels (1) and (2) are then blended respectively at a ratio of 70:30 and the pH of the blend is adjusted to approximately 5 pH using ~0.6% sodium bicarbonate. Additional sodium sulfate may be added to the blend at a level of ~1.2%. The FIGURE illustrates the above process. The acronyms in the FIGURE have the following meanings.

TV=total volatiles
APS=median particle size
GPM=gallons per minute
H=hours

EXAMPLE 2

Cleaning Performance

The silicas of Example 1 and those indicated below were incorporated into a conventional dentifrice composition and then evaluated for PCR and RDA. The results are provided below.

Powders of the abrasive from Example 1 (Powder A), and two other silicas (Powder B and Powder C) were evaluated for Einlehner abrasion. The results are provided below.

|  | PCR | RDA |
|---|---|---|
| Dentifrice A (containing Sylodent ® 783 and invention)[1] | 101 | 124 |
| Dentifrice B (containing invention)[2] | 107 | 120–150 |
| Dentifrice C (containing Sylodent ® 783 alone)[3] | 72 | 117 |
| Dentifrice D (containing commercially available precipitated silica abrasive)[4] | 72 | 83 |

| Einlehner Abrasion | |
|---|---|
| Powder A (invention)[5] | 0.6–1.6 |
| Powder B (Sylodent ® 783)[6] | 1.2 |
| Powder C (precipitated silica silica abrasive)[7] | 6.4 |

[1]Dentifrice (A) is a toothpaste containing humectant (42% by weight sorbitol, 12% by weight glycerin and 3% by weight polyethylene glycol), 15% water, and 11% by weight Sylodent 783 commercially available from W. R. Grace & Co.-Conn. and 10% by weight silica prepared according to Example 1. The remaining balance of ingredients include carboxymethylcellulose, fluoride, titania, thickener, surfactant, and tetrasodium phosphate, and flavoring.
[2]Dentifrice (B) is the toothpaste of (A) containing 20% by weight silica of Example 1.
[3]Dentifrice (C) is the toothpaste of (A) containing 20% Sylodent ® 783.
[4]Dentifrice (D) is the toothpaste of (A) containing 20% by weight of a precipitated silica abrasive.
[5]Powder A is a silica prepared according to Example 1.
[6]Powder B is Sylodent ® 783 abrasive.
[7]Powder C is a precipitated silica abrasive.

What is claimed:

1. An amorphous silica gel composition comprising a particulate having:

(a) a median particle size in the range of about 5 to 12;
   (b) bronze screen Einlehner hardness of about 0.1 to 3;
   (c) total volatiles content of about 20 to about 40% by weight based on the weight of silica; and
   (d) a pH of about 3.0 to 6.0;
   wherein said particulate comprises a mixture of at least two different silica gel abrasives.

2. The composition of claim 1 wherein (a) is in the range of about 7 to 10 microns.

3. The composition of claim 1 wherein (b) is in the range of about 0.5 to about 2.0.

4. The composition of claim 1 wherein (c) is about 25 to 35%.

5. The composition of claim 1 wherein the particulate consists essentially of silica gel.

6. A dentifrice composition comprising 0.1 to 99%, by weight of said composition, of an orally-acceptable carrier and an amorphous silica gel abrasive,
   (1) the abrasive having a:
      (a) a median particle size in the range of about 5 to 12 microns;
      (b) bronze screen Einlehner hardness of about 0.1 to 3;
      (c) total volatiles content of about 20 to about 40% by weight based on the weight of silica; and
      (d) a pH of about 3.0 to 6.0; and
   (2) the dentifrice composition having a Pellicle Cleaning Ratio of at least 80;
   wherein said abrasive comprises a mixture of at least two different silica gel abrasives.

7. The dentifrice composition of claim 6 wherein the abrasive (1) consists essentially of silica gel.

8. The dentifrice composition of claim 6 wherein (c) is in the range of about 25 to about 35%.

9. The dentifrice composition of claim 6 wherein (a) is in the range of 7 to about 10 microns.

10. The dentifrice composition of claim 6 wherein the dentifrice has a PCR of at least 100.

11. The dentifrice composition of claim 6 wherein the silica abrasive comprises about 10 to about 25% of the composition's total weight.

* * * * *